United States Patent
Harris et al.

(10) Patent No.: US 6,541,243 B1
(45) Date of Patent: Apr. 1, 2003

(54) PERFUSION CHAMBER FOR ELECTROPHYSIOLOGICAL TESTING OF OOCYTES

(75) Inventors: Eric W. Harris, Worcester, MA (US); Thomas H. Lanthorn, Pittsford, NY (US); Maurice A. Kildal, Webster, NY (US)

(73) Assignee: Axon Instruments, Inc., Union City, CA (US)

( * ) Notice: Subject to any disclaimer, the term of this patent is extended or adjusted under 35 U.S.C. 154(b) by 119 days.

(21) Appl. No.: 09/586,633

(22) Filed: Jun. 5, 2000

(51) Int. Cl.$^7$ .............................. C12M 3/00; C12Q 1/02
(52) U.S. Cl. ................ 435/285.1; 435/29; 435/297.2; 435/287.1; 435/288.4; 435/288.7; 436/63
(58) Field of Search .............................. 435/29, 30, 32, 435/33, 40.51, 287.1, 287.7, 287.9, 288.4, 288.7, 297.5, 297.2, 285.1, 284.1, 305.1, 307.1; 359/398; 436/63; 206/521.2, 521.8, 521.9; 269/900

(56) References Cited

U.S. PATENT DOCUMENTS

| | | | |
|---|---|---|---|
| 4,395,492 A | 7/1983 | Rees | 435/283 |
| 4,681,853 A | 7/1987 | Hardy et al. | 435/288 |
| 4,762,794 A | 8/1988 | Nees | 435/284 |
| 4,889,691 A | 12/1989 | Argentieri | 422/102 |
| 4,894,343 A * | 1/1990 | Tanaka et al. | 210/498 |
| 5,043,260 A | 8/1991 | Jauregui | 435/1 |
| 5,056,464 A * | 10/1991 | Lewis | 119/6.8 |
| 5,126,034 A | 6/1992 | Carter et al. | 204/403 |
| 5,262,128 A * | 11/1993 | Leighton et al. | 296/107.09 |
| 5,449,492 A * | 9/1995 | Krishtal | 422/63 |
| 5,496,697 A * | 3/1996 | Parce et al. | 435/29 |
| 5,505,721 A | 4/1996 | Leach et al. | 604/403 |
| 5,506,141 A * | 4/1996 | Weinreb et al. | 422/101 |
| 5,541,081 A * | 7/1996 | Hardy et al. | 435/25 |
| 5,565,353 A | 10/1996 | Klebe et al. | 435/240.25 |
| 5,759,846 A | 6/1998 | Stoppini et al. | 435/284.1 |
| 6,048,722 A * | 4/2000 | Farb et al. | 435/286.5 |
| 6,054,287 A * | 4/2000 | Gao et al. | 435/29 |
| 6,187,053 B1 * | 2/2001 | Minuth | 128/898 |
| 6,197,575 B1 * | 3/2001 | Griffith et al. | 435/288.4 |
| 6,303,375 B1 * | 10/2001 | Kimura et al. | 435/177 |

FOREIGN PATENT DOCUMENTS

| | | | |
|---|---|---|---|
| DE | 40 04 198 A | * | 8/1991 |
| WO | WO-96/13721 A1 | * | 5/1996 |

* cited by examiner

*Primary Examiner*—William H. Beisner
(74) *Attorney, Agent, or Firm*—Antonio R. Durando; Durando Birdwell & Janke, PLLC (57) ABSTRACT

A perfusion chamber includes a porous oocyte support structure. A continuously sloped top surface and a receiving well in the support structure entrap the underside of the oocyte, thereby localizing the cell in a predetermined fixed position within the reach of dedicated voltage-clamp microelectrodes. A test solution is delivered continuously at the top of the chamber, above the oocyte, and withdrawn from the bottom of the chamber, below the oocyte. The porosity of the support material enables the continuous perfusion of test solution around the membrane of the oocyte, including its bottom portion that is held firmly in contact with the holding well. The geometry of the holding well is selected such as to ensure the automatic and precise placement of the oocyte by gravity and to optimize the pressure distribution over its membrane, thereby minimizing the probability of rupture or other damage to the cell. The entire top surface of the support structure is sloped inward toward the substantially central well, and the bottom of the well is contoured to conform to the shape of an oocyte of average size.

40 Claims, 9 Drawing Sheets

PERFUSION CHAMBER FOR ELECTROPHYSIOLOGICAL TESTING OF OOCYTES

BACKGROUND OF THE INVENTION

1. Field of the Invention

This invention is related in general to holding chambers for carrying out identification of targets in the drug discovery process and, in particular, to a perfusion chamber for measuring electrophysiological responses from frog oocytes.

2. Description of the Related Art

The modern process of drug discovery involves a number of distinct steps. Various possible sources for drugs are first investigated to generate libraries of compounds to test for potential activity. Such compounds are preferably produced using combinatorial chemistry, and are typically synthesized from theoretical considerations or on the basis of templates derived from natural products harvested from around the world and previously tested for activity. These libraries of compounds are then screened to assess their effects on particular targets of interest. As used in the art, "targets" are the entities acted upon by drugs, normally proteins and receptors that transmit information within and between cells and tissues. Targets are first identified by locating them within any biochemical pathway that is relevant to a disease, and they are then validated by showing that their modification produces an effect on the disease.

These libraries of compounds are screened through assays that involve a predetermined protocol for a biochemical reaction to occur that leads to definitive information about the activity of the screened compound on the target. When an active compound is found (normally called a "hit" in the art), second-pass screenings are conducted to test for low toxicity and good chemical and physical properties. The compounds that successfully emerge from these multiple screenings (called "leads") are then tested on animals to determine their physiological effects and, if warranted, are finally tested on humans through clinical trials.

The ability to develop screening assays rapidly and to screen compound libraries at high throughput is becoming increasingly critical in the discovery of new drugs, which is now a large-scale industrial activity. The explosion of data made available from the Human Genome Project coupled with advances in chemical synthesis has produced a great demand for ever-higher screening rates to test potentially therapeutic compounds. Therefore, there is a growing need for integrated laboratory systems that assess large numbers of compounds quickly.

Of particular relevance to the present invention are assays conducted on Xenopus frog oocytes, which are uniquely suitable for screening of ion channels linked to a variety of diseases. Using conventional voltage clamping across the membrane of the oocyte, the voltage dependence of ion channel activity in the oocyte cell is assessed by measuring current changes produced in response to exposure to multiple test solutions. Testing of an oocyte cell under voltage-clamped conditions, a well known technique in the art, is carried out in a batch operation in a chamber designed to support an individual oocyte being perfused with a test solution. The cell membrane is pierced with two microelectrodes of a voltage-clamp amplifier capable of recording current variations in response to voltage step changes or to the application of compounds under constant-voltage conditions. A conventional two-electrode voltage-clamp system 10 is illustrated schematically in FIG. 1, where numerals 12 and 14 refer to a voltage-recording microelectrode and a current-passing microelectrode, respectively, inserted through the membrane 16 of an oocyte cell C. The membrane potential $V_m$ is recorded by a unit-gain buffer amplifier 18 connected to the microelectrode 12. The membrane potential $V_m$ is compared to a control potential $V_c$ in a high-gain differential amplifier 20 (with gain $\mu$) producing a voltage output $V_\epsilon$ proportional to the difference $\epsilon$ between $V_m$ and $V_c$. The voltage $V_\epsilon$ at the output of the differential amplifier 20 forces current to flow through the current-passing microelectrode 14 into the oocyte cell C, such as to drive the error $\epsilon$ to zero and maintain the membrane voltage clamped at $V_c$.

Figure 1:
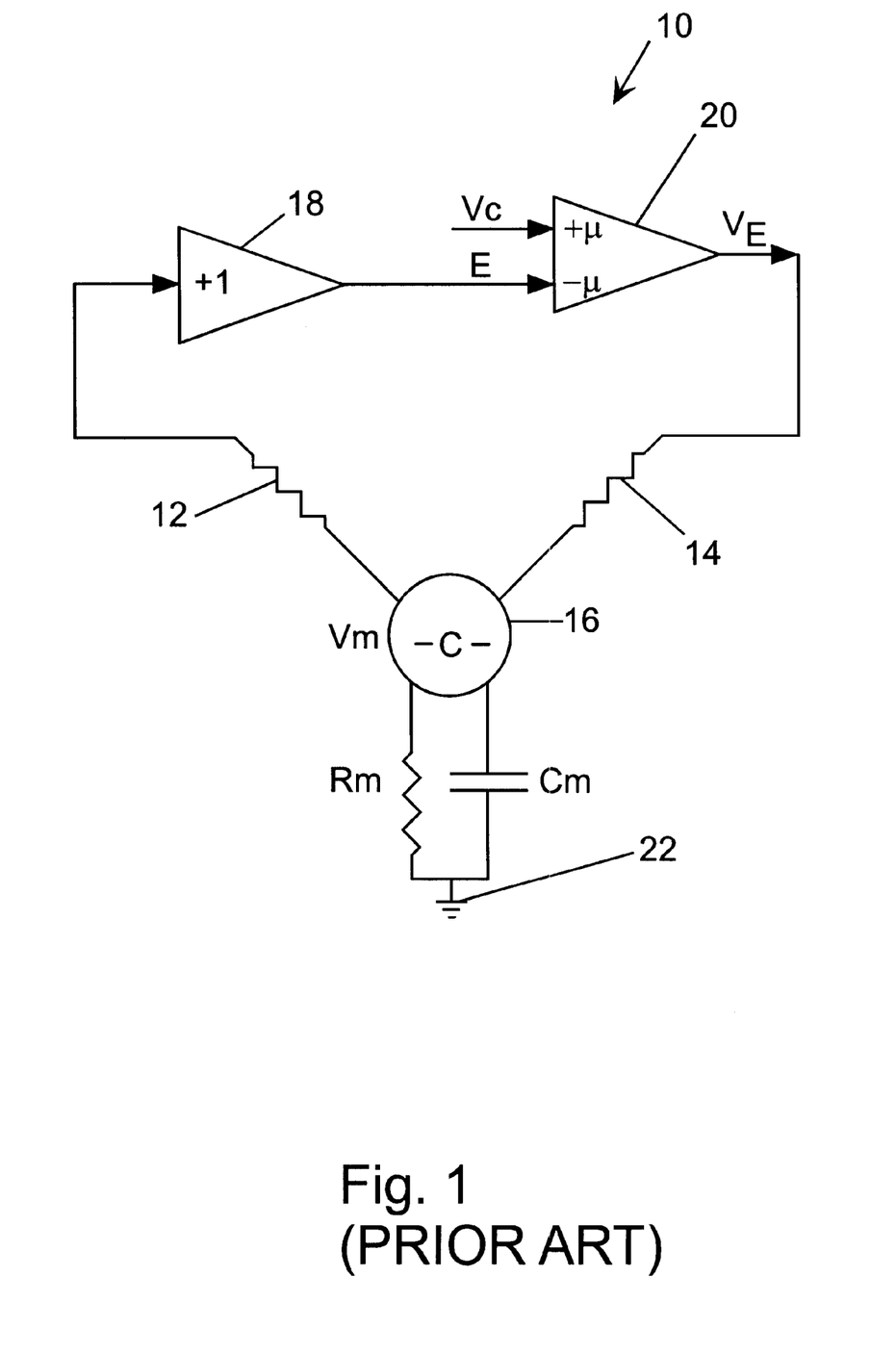
FIG. 1 is a schematic diagram of a conventional two-electrode voltage-clamp circuit applied to a cell in a test chamber.

The circuit is completed through a ground 22 across the cell membrane, which in the schematic is modeled by impedance and capacitance values $R_m$ and $C_m$, respectively.

The primary concerns of designs of perfusion chambers for oocytes are the isolation of the cell in a stationary condition and the ability to expose it to the test solution of interest. Some chamber designs have involved trapping and flooding the oocyte in a retaining structure, such as in the mesh of a web material suspended above the bottom of the chamber. Once so restrained, the oocyte is connected to the voltage-clamp microelectrodes and perfused with test solution in a batch operation.

Most prior-art perfusion chambers are directed to particular tissues and cell layers, rather than individual cell material. See, for example, U.S. Pat. Nos. 4,762,794, 5,043,260, and 5,565,353.

In addition, prior-art perfusion chambers are designed for carrying out tests using individual workstations, performing one experiment at a time. The configuration of the chamber often impedes direct access to the oocyte, thereby complicating automatic insertion of the electrodes. The structure supporting the oocyte does not always permit exposure of its entire membrane to the test solution, which is an important test factor for pharmacological studies of voltage-gated channels, for instance).

Moreover, considerable skill and manipulation is required to place the oocyte in the appropriate position within the chamber, which is prohibitive for automated, rapid-throughput, parallel-testing applications. Finally, the geometries of the structures used to support the oocytes in prior-art chambers have not been optimized to reduce damage to the cells; and the delivery of perfusion solutions has not been engineered for multiple, sequential testing in a continuous operation. Accordingly, the prior-art chambers are not well suited for the high-throughput, electronically manipulated, automated-system needs of today's pharmaceutical industry. This invention provides a simple solution to address these needs.

BRIEF SUMMARY OF THE INVENTION

The primary objective of this invention is a perfusion chamber suitable for sequential testing of an animal cell through successive exposures to multiple perfusion solutions in an automated, continuous system.

Another objective is a chamber that permits the continuous perfusion of the cell in an environment wherein its entire membrane is exposed to the test solution.

Another goal of the invention is a design particularly suitable for the testing of oocytes, especially Xenopus oocytes.

Still another objective is a perfusion chamber design that can be adapted for parallel testing of multiple oocytes in a high-throughput testing system.

Another goal is a perfusion chamber that is suitable for implementation within an automated voltage-clamp and solution-delivery system.

Yet another object is a system that can be implemented using conventional voltage-clamp hardware and software, modified only to the extent necessary to meet the design parameters of the chamber of the invention.

Still another goal is a method of perfusion that facilitates the rapid, sequential testing of an oocyte with multiple test solutions on a continuous basis.

A final objective is a system that can be implemented economically according to the above stated criteria.

Therefore, according to these and other objectives, one aspect of the present invention lies in a perfusion chamber that includes a porous oocyte support structure. A continuously sloped top surface and a receiving well in the support structure produce the automatic entrapment of the underside of the oocyte, thereby localizing the cell in a predetermined fixed position within the reach of dedicated voltage-clamp microelectrodes. The test solution is delivered continuously at the top of the chamber, above the oocyte, and withdrawn from the bottom of the chamber, below the oocyte. The porosity of the support material enables the continuous perfusion of test solution around the membrane of the oocyte, including its bottom portion that is firmly in place within the holding well.

According to another aspect of the invention, the geometry of the holding well is selected such as to ensure the automatic and precise placement of the oocyte by gravity and optimize the pressure distribution over its membrane, thereby minimizing the probability of rupture or other damage to the cell. To these ends, in the preferred embodiment of the invention the entire top surface of the support structure is sloped inward toward the substantially central holding well, and the bottom of the well is contoured to conform to the shape of an oocyte of average size.

Various other purposes and advantages of the invention will become clear from its description in the specification that follows and from the novel features particularly pointed out in the appended claims. Therefore, to the accomplishment of the objectives described above, this invention consists of the features hereinafter illustrated in the drawings, fully described in the detailed description of the preferred embodiment and particularly pointed out in the claims. However, such drawings and description disclose but one of the various ways in which the invention may be practiced.

DESCRIPTION OF THE PREFERRED EMBODIMENTS OF THE INVENTION

The heart of this invention lies in the idea of utilizing a sufficiently porous material to support an oocyte in a perfusion chamber so as to permit its total exposure to the continuous, uniform perfusion of its membrane with a test solution. Further, the geometry of the support site is optimized to facilitate the introduction of the oocyte, to evenly distribute the pressure exerted on the oocyte's membrane by the support structure, and to firmly place the oocyte within the automatic reach of voltage-clamp hardware. These improvements have enabled the implementation of a multiple-chamber, continuous-operation, automated electrophysiology recording device.

Figure 2:
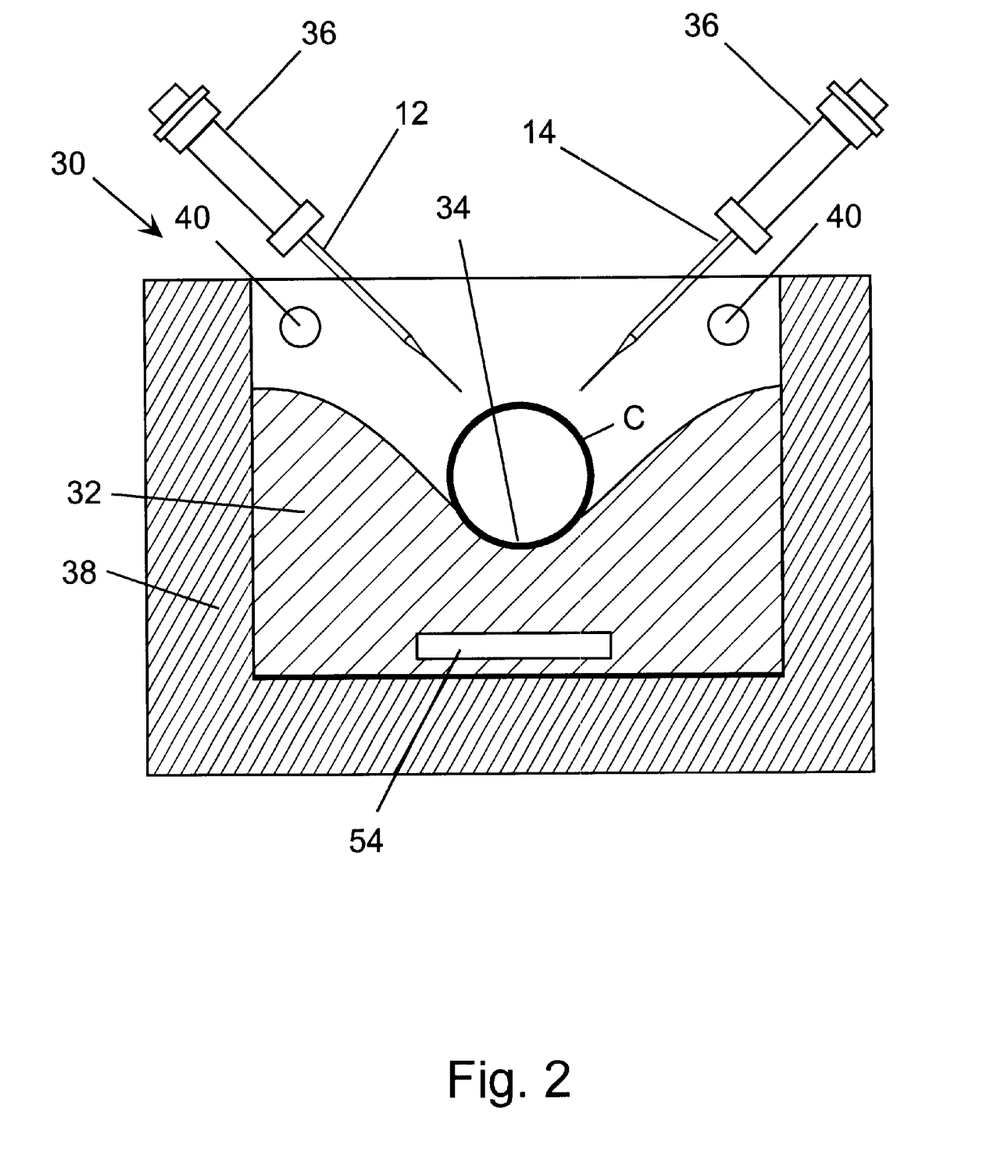
FIG. 2 is a schematic, cross-sectional, elevational view of a perfusion chamber according to the invention showing an oocyte cell secured in position in a test well for voltage-clamp perfusion measurements.
Figure 3:
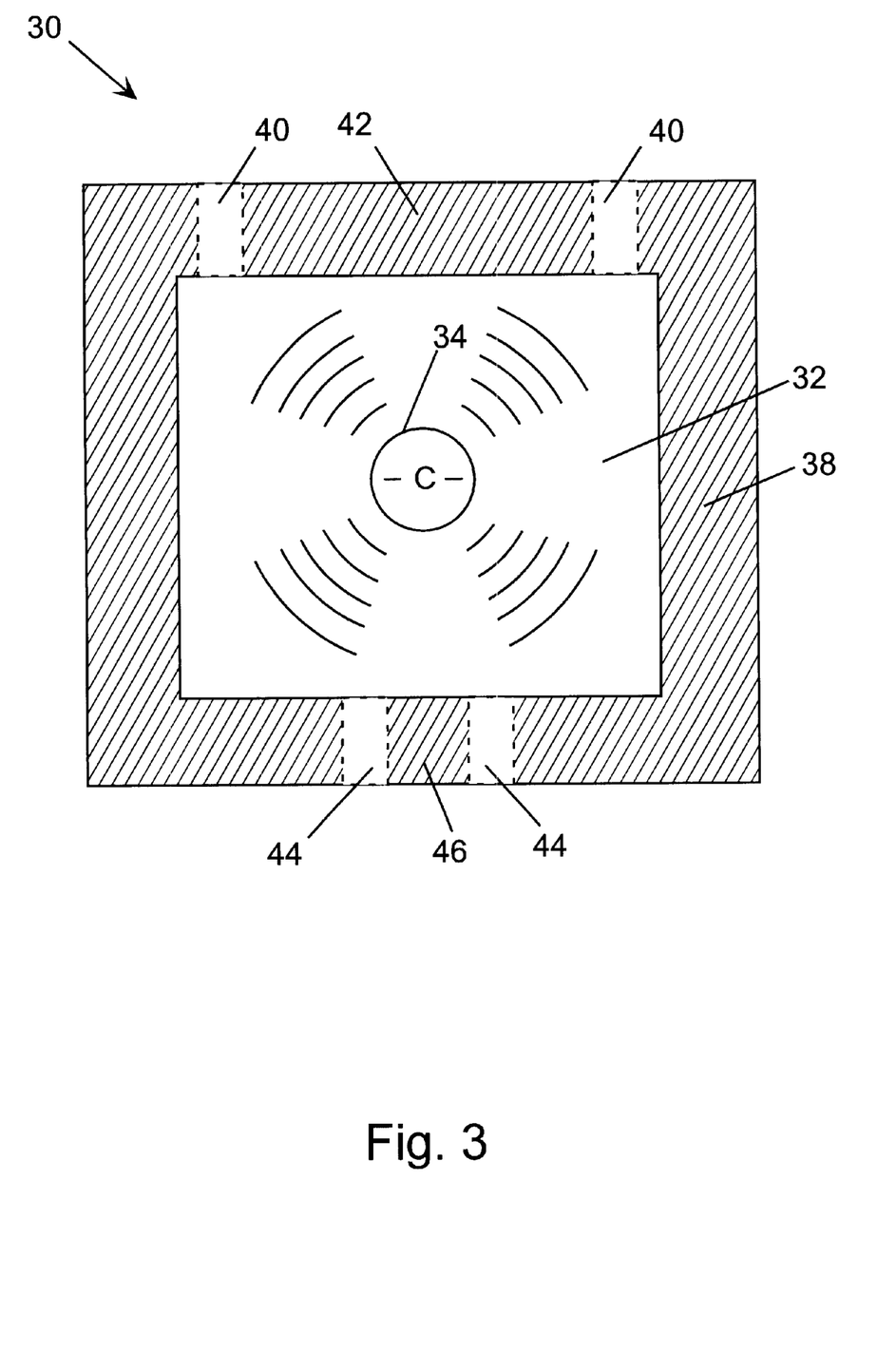
FIG. 3 is a schematic top view of the chamber of FIG. 2 illustrating the perfectly rounded horizontal sections, gradually decreasing in diameter toward the bottom, of the geometry of the well.

Referring to the figures, wherein the same reference numerals and symbols are used throughout for like parts, FIG. 2 is a sectioned schematic illustration of a perfusion chamber 30 according to the invention. The drawing shows a porous support structure 32 in a vertical section through the center of a holding well 34 sized for retaining an oocyte cell C of average size. As also illustrated by the curvature shading shown in the top schematic view of FIG. 3, the well 34 consists of a crater with perfectly round horizontal cross-sections of gradually decreasing diameter toward a centered bottom. Similarly, the rest of the support structure 32 has a sloped top surface progressively converging downward toward the holding well.

Thus, the convergence of each side of the support structure 32 toward the central bottom of the crater produces the automatic gravitational placement of the oocyte in a predetermined assured position that permits the repetitive and consistent placement of voltage-clamp microelectrodes 12,14 into the oocyte. As shown, the microelectrodes are suspended over the chamber 30 and connected to a support frame 36 adapted to move the electrodes forward or backward along a precisely controlled path in the direction of the cell being tested. The mechanisms used to place the microelectrodes through the cell membrane are not part of the present invention and are well known in the art; therefore, they are not described in detail here.

In order to minimize the probability of damage to the oocyte's membrane after placement within the well 34, the geometry of bottom portion of the well is designed so as to distribute the pressure exerted on the membrane as evenly as possible. The contour of the well is shaped to envelop the natural profile of the cell, which, in the case of an oocyte, tends to be substantially spherical. Since a different profile would be required to fit cells of different sizes, a geometry for an average cell size is selected. Xenopus oocytes, the most frequently used cells for certain types of target screening, tend to vary between 0.8 and 1.5 mm in diameter. Accordingly, the preferred geometry of the bottom portion of the well 34 conforms to the surface of a sphere with a radius of about 0.6 mm. Similarly, the depth of the well 34 is preferably selected to ensure that the top of the largest oocyte, once in place, is aligned with or below the highest point of the support structure's top surface while retaining open access by the microelectrodes 12,14. To this end, the preferred slope of the well 34 and of the surrounding surface is limited to a minimum of 35 degrees and a maximum of 44 degrees, an average of 40 degrees being preferred for average applications. This feature has been found to provide great stability to the placement of the oocyte during perfusion.

The porous support structure 32 is housed in an impermeable shell 38 through which the perfusion solution is delivered and withdrawn. Input ports 40 are located in a wall 42 of the shell 38 above the elevation expected to be reached by the largest cell under testing to ensure that the cell is completely immersed in the test solution. Output ports 44 are similarly located in a wall 46 (FIG. 3) substantially at the bottom of the shell 38 for removing the test solution perfused around the membrane of the oocyte cell C. According to the main novel aspect of the invention, the solution flow path from the well 34 to the output ports 44 is by gravity and through the pores of the material constituting the support structure 32. Therefore, it is critical that the porosity of this material be sufficient to permit gravitational flow rates of the magnitude required by the experimental parameters of the perfusion chamber. For electrophysiology recording involving oocyte cells, typical rates are about 2–4 ml/min. Accordingly, materials having a preferred pore size of about 15–45 microns have been found to be suitable to practice the invention. In particular, rigid ceramics (such as the $Al_2O_3$-based ceramic Kellundite® manufactured by Filtros Ltd. of East Rochester, N.Y.) with an average porosity of 40% and pore size of 15–40 microns, 20 microns being preferred, are used for their relative facility of manufacture with precise dimensions and their ability to retain the original shape of the well. On the other hand, more flexible, resilient materials, such as the porous polyethylene sold under the trademark POREX® by the Porex Company of Fairburn, Ga., with an average pore size of 15–45 microns, is preferred for applications that require a softer support surface, even though such materials are relatively difficult to shape during manufacture and tend to lose their initial configuration over time.

In operation, the chamber 30 of the invention is used to reliably and automatically trap an oocyte C in its well 34 for full exposure to a test solution introduced at a predetermined flow rate into the top of the chamber through the inlet ports 40. Because the retaining surface of the chamber (the well 34) and the entire mass of the support structure 32 consist of porous material, the fluid flows by gravity to the bottom of the chamber from where it is removed through the output ports 44. This flow pattern through a highly porous material not only produces uniform bathing of the oocyte, but also tends to keep the oocyte in place, thereby further facilitating the process of electrode penetration and removal. Moreover, rapid and complete changeover of perfusion solutions is also enhanced to the advantage of automated utilization.

Figure 4:
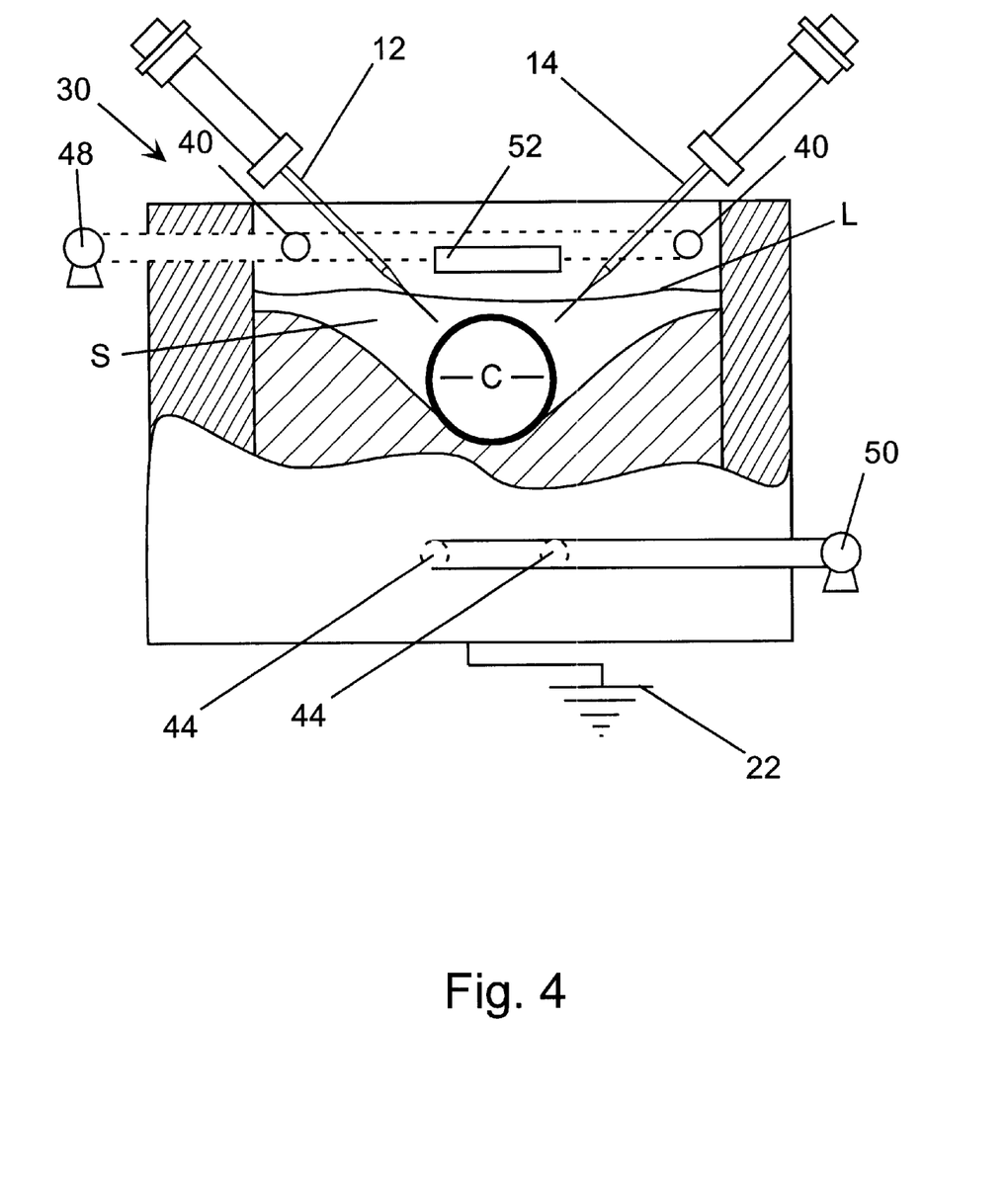
FIG. 4 is a partially sectioned view of the chamber of FIG. 2 showing inlet and outlet plumbing and an aspirator to remove excess liquid in the chamber.

As illustrated schematically in FIG. 4, in order to ensure that the perfusion solution S is exchanged uniformly throughout the chamber, that it bathes the entire oocyte, that the chamber never runs dry (which would lead to oocyte rupture), and that the fluid flows at a known reproducible rate (so that the amount of solution needed for a given length of drug application is known), the solution is preferably pumped into the chamber 30 at a given rate by a constant-flow pump 48 (such as with a peristaltic pump). The fluid is then pumped out of the bottom of the chamber at a slightly lower rate by another constant-flow pump 50, thereby ensuring that the oocyte is always fully immersed in solution. For example, pump 48 may deliver fluid at 2.0 ml/min while pump 50 removes it at 1.8 ml/min. The excess volume is preferably removed by an aspirator 52 positioned just above the chamber 30. When the fluid level L reaches an elevation sufficiently close to the aspirator 52, it is removed until the level drops below its reach, and then it begins to slowly rise again. Obviously, the reach of the aspirator 52 must be calibrated to ensure that the fluid level L always remains above the oocyte.

Since the oocyte C is automatically placed at the center of the well 34, the microelectrodes 12,14 can also easily be targeted to the oocyte for automatic operation, and no impediments exist to their direct penetration (such as the netting material utilized to fix oocytes in prior-art chambers). Thus, the microelectrodes can be advanced automatically until penetration is detected by a negative change in the voltage measured with respect to a ground plate 54 at the bottom of the chamber (see FIG. 2), which in turn is electrically connected to an exterior ground 22. (Note that the amplitude of the current varies with the type of protein being expressed and the composition of the perfusion solution applied to the oocyte.)

Figure 5:
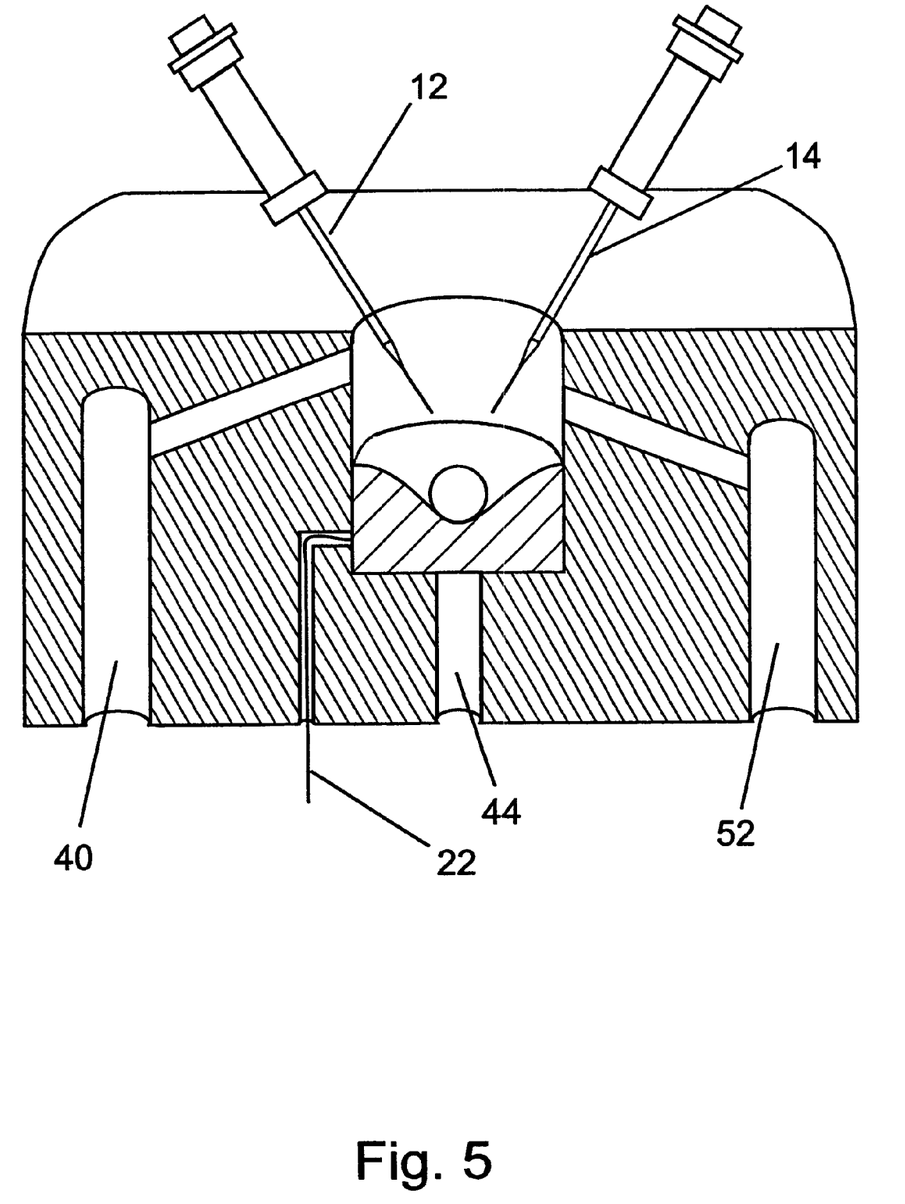
FIG. 5 is a partial sectional view of a device comprising the preferred embodiment of a perfusion chamber according to the invention.

FIG. 5 is an enlarged, partial section of the perfusion chamber of the invention, seen looking down from the front, as implemented in a prototype. In this embodiment, the aspirator 52 consists either of an aspirated port, or an aspirated port including a wick, or even simply a wick absorbing fluid by capillarity.

Figure 6:
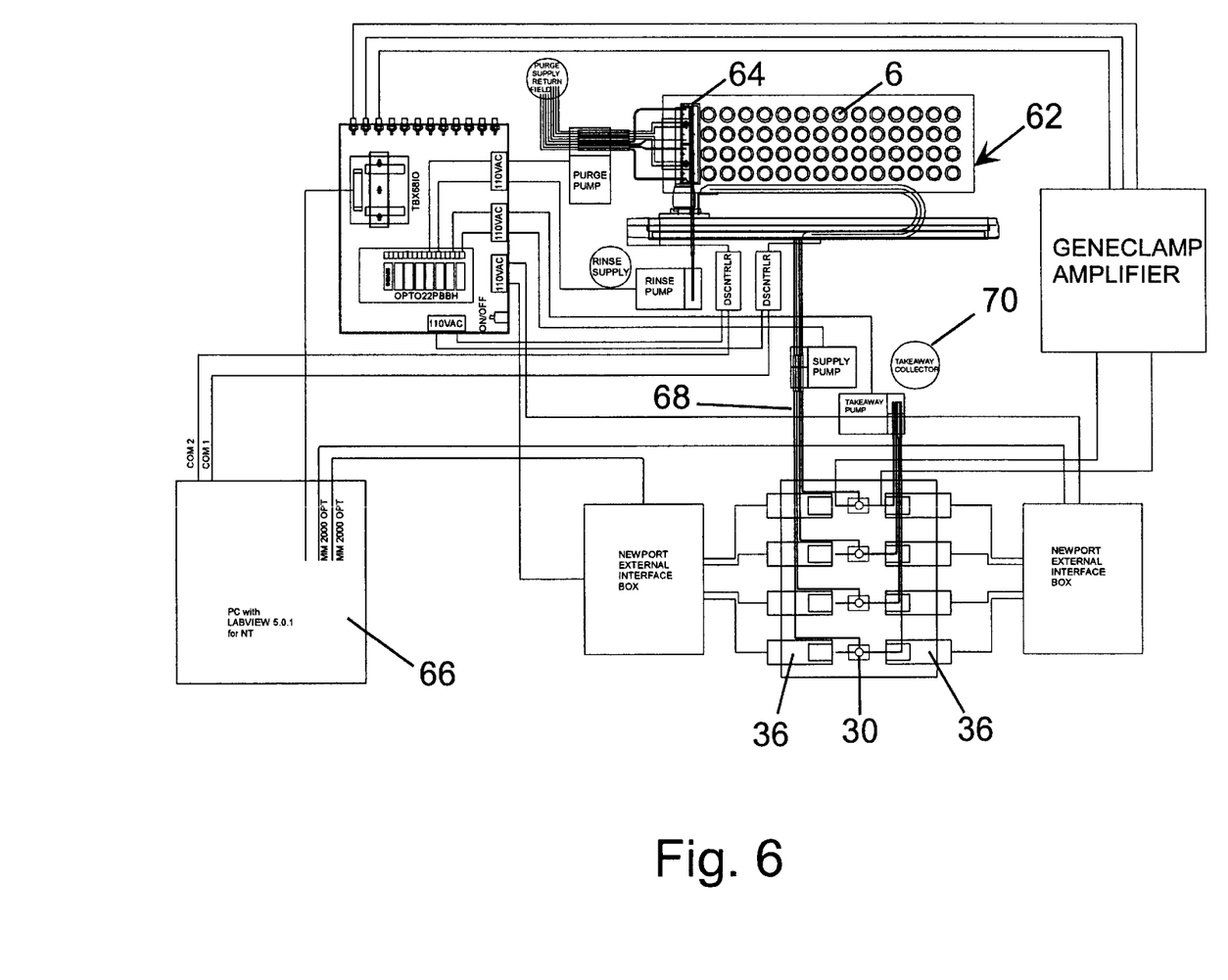
FIG. 6 is a schematic illustration of a four-unit automated system for carrying out multiple, sequential experiments in parallel.

The viability of the chamber 30 of the invention for a multiple-unit, parallel-testing perfusion apparatus was successfully investigated. As illustrated schematically in FIG. 6, four perfusion chambers 30 were mounted in a row within corresponding sets of microelectrode pairs 12,14 aligned with the chamber wells 34. Test fluids, to be independently applied to the oocytes placed in the four chambers, were pumped from separate vials 60 arranged in an array 62. The supply tubing was placed in any given vial using a "pick and place" two-dimensional robotic positioner 64 under control of a computer 66. The positioner had sufficient range to reach and apply at least ten different solutions during an experiment. Scintillation vials were chosen as vessels for the test solutions. They are inert, inexpensive, resealable, and hold a sufficient volume of solution (about 20 ml) to permit up to 5 minutes of application at a rate of 4 ml/min (a maximum desirable flow rate for oocyte recordings).

Figure 7:
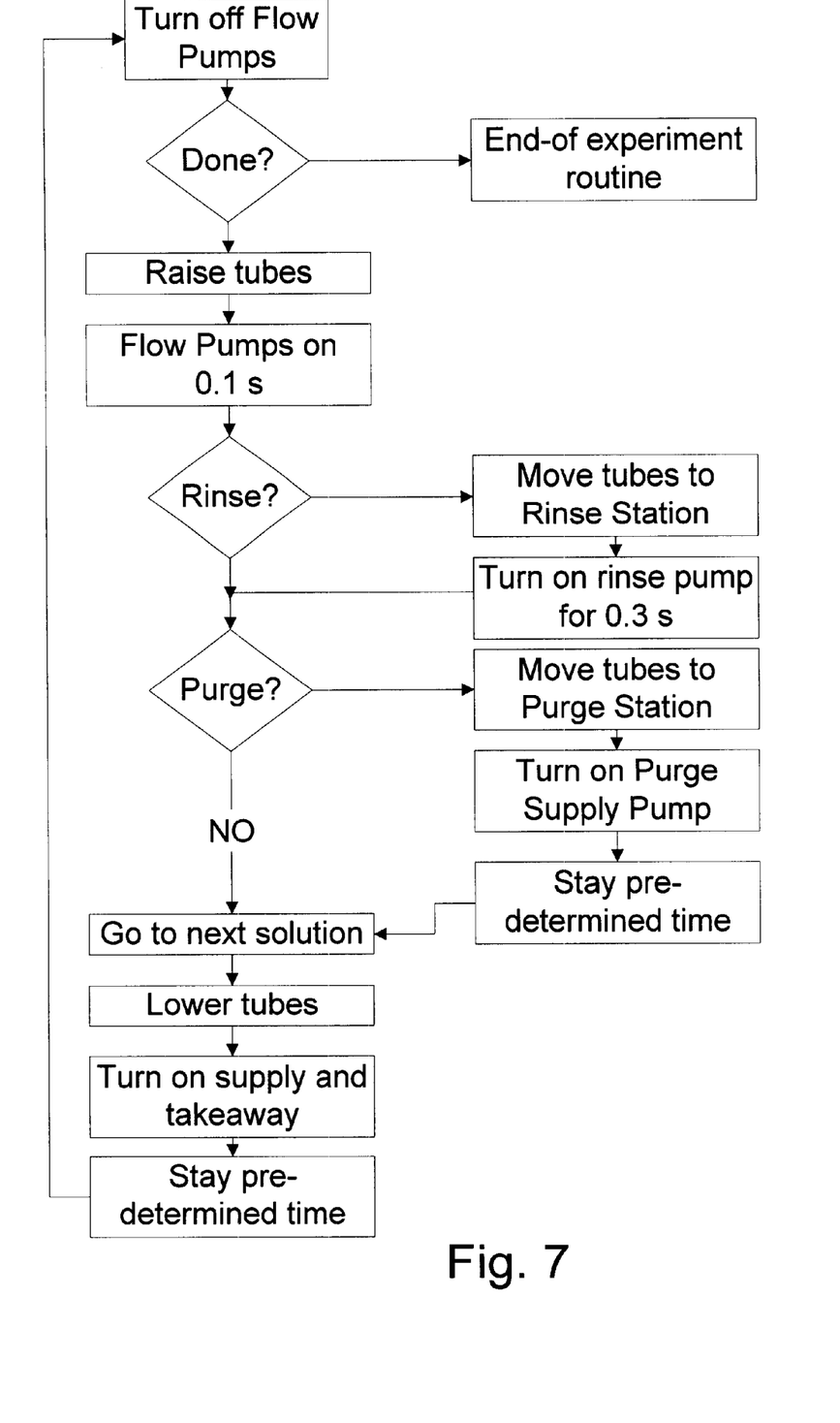
FIG. 7 is a flow-chart of the steps involved during each cycle of fluid application using the system of FIG. 65.

Separate supply lines and reservoirs 68 were used to ensure electrical isolation between the fluids bathing each chamber, and used fluids were dripped into a single waste container 70. To prevent cross-contamination between different test solutions, the supply tubes were passed through a "spray station" where a jet of cleaning fluid was used to rinse the outer surface of the tubes. Test solutions were administered in parallel to each of the four chambers and additional tests were performed sequentially by repeating the cycle. In addition, an air bubble was introduced in each supply line before each change of solution to prevent mixing of solutions in the vials and in each supply line in transit toward a chamber. Although not present in this embodiment of the invention, a purge system might be desirable to wash off drugs from the feed lines between application cycles. FIG. 7 is a flow-chart of the steps involved during each cycle of fluid application, which were implemented automatically using the chamber of FIG. 5 and the multiple-unit apparatus of FIG. 6.

Figure 8:
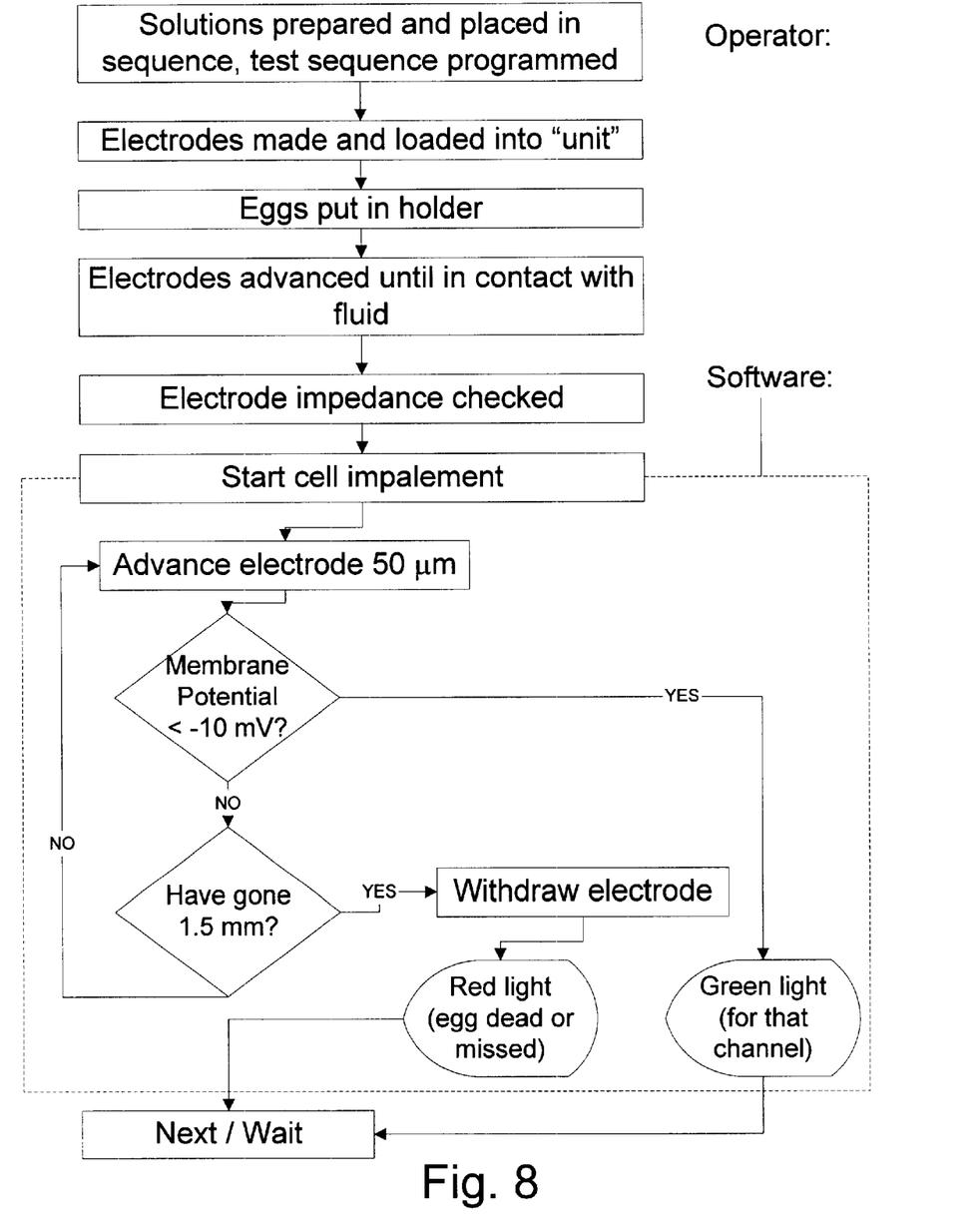
FIG. 8 is a flow-chart of the sequence of steps followed for automatically positioning the voltage-clamp electrodes into the oocytes in the system of FIG. 6.

The voltage-clamp system was controlled with conventional two-axis positioners. Based on the precise geometry of the chambers, the electrodes were initially positioned automatically within less than about 100 μm of the oocyte's membrane and then advanced until a voltage change of at least about 10 mV in the recorded voltage indicated cell penetration. Oocytes are typically about 1.1 mm in diameter and penetration normally occurs within about 400 μm of first contact with a microelectrode. Therefore, this distance could be advantageously estimated for quick, automated application as a result of the reproducible placement of the oocytes within the perfusion chamber, as afforded by the invention. FIG. 8 illustrates in flow-chart form the sequence followed for automatically positioning the voltage-clamp electrodes into the oocytes.

Figure 9:
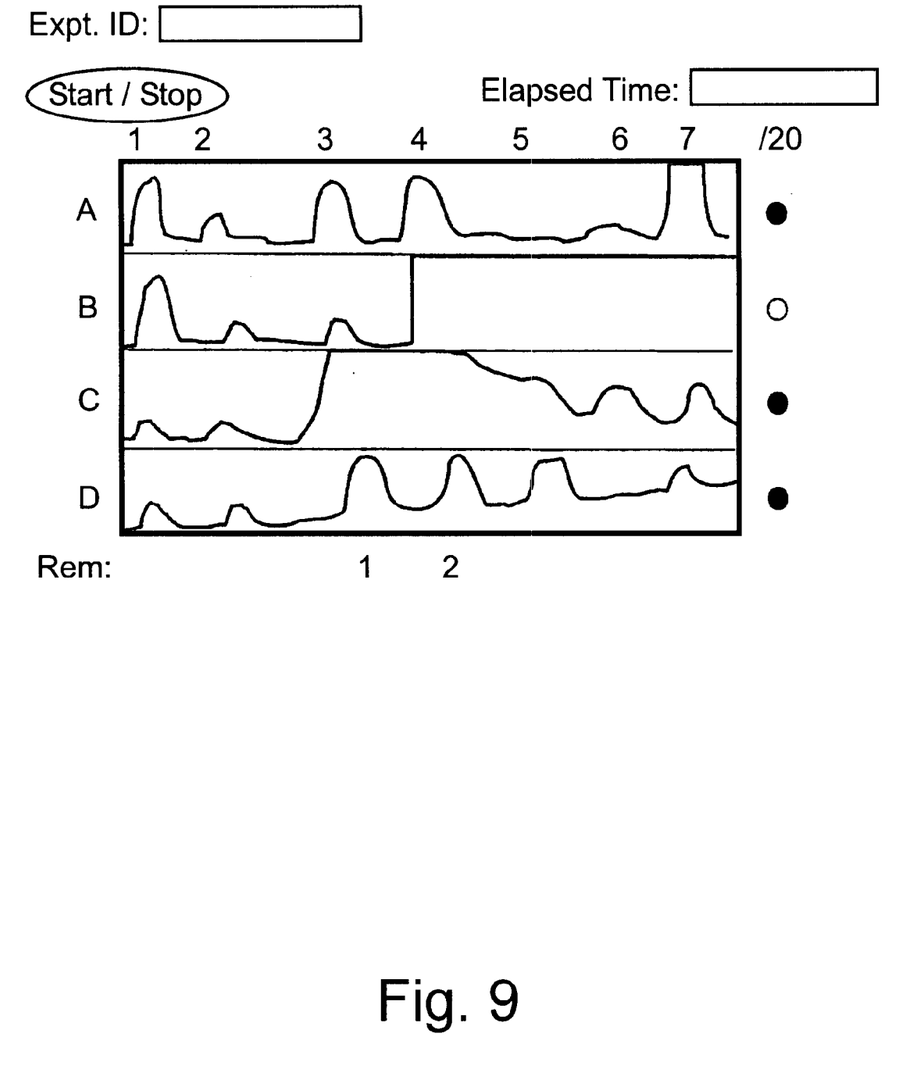
FIG. 9 is an example of data that might be collected during serial solution applications using the system of FIG. 6.

FIG. 9 is an example of data that might be collected during serial "agonist applications" using the system of the invention. The data show results from seven sequential experiments run in each of four chambers (designated A,B, C,D). Note that chamber B shows a failure starting at experiment 4, where the baseline current jumps as would be seen if an egg were to rupture. As well understood by those skilled in the art, the current amplitude response in each application is relevant to the information sought.

Thus, it has been demonstrated that the perfusion chamber of the invention is suitable for automating the parallel, high-throughput, recording process of oocyte electrophysiology experiments. The chamber made it possible to test multiple oocytes in parallel; to automate electrode penetration into the oocyte; and to automate fluid delivery to the chambers. It is anticipated that data analysis will also be automated, thereby further improving throughput. A very desirable goal is also the automation of oocyte injection and preparation, which would provide additional efficiency to the process.

In fact, the open top and the surface configuration of the support structure of the invention is particularly suitable for combining preparatory microinjection and electrophysiological recording of oocytes in the same chamber, thereby eliminating the undesirable need for transferring the oocytes between test sites. We found that, once placed in the holding well of the invention, the oocyte is sufficiently anchored to the bottom of the chamber to be pierced with microinjection apparatus from the open top of the chamber. After treatment, the oocyte can be allowed to incubate in place for the appropriate period of time, after which electrophysiology experiments can be carried out in the same chamber. Thus, the entire process of recording can be conducted without moving the oocyte after its original placement in the well of the invention.

Various changes in the details, steps and components that have been described may be made by those skilled in the art within the principles and scope of the invention herein illustrated and defined in the appended claims. For example, the invention has been described in terms of a perfusion chamber for oocytes, but the same inventive principles would apply for any other type of cell or other material that can be advantageously held in a chamber well of the type disclosed. Similarly, the porosities described above, while optimal for the disclosed perfusion rates relevant to oocytes, could easily be varied and adjusted to provide different rates for other electrophysiology experiments. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of the claims so as to embrace any and all equivalent apparatus and procedures.

We claim:

1. A perfusion chamber for an electrophysiology recording device, comprising:
    an impermeable shell with a top portion defining a single liquid compartment and a bottom portion;
    a porous support structure occupying said bottom portion of the shell below said liquid compartment;
    a holding well formed in the support structure for receiving a material subjected to an electrophysiologic experiment;
    an input port for supplying a perfusion solution to the material held in the well; and
    an output port for removing the perfusion solution directly from the porous support structure.

2. The chamber of claim 1, wherein said porous support structure includes a porous ceramic with an average pore size between 15 and 40 microns.

3. The chamber of claim 1, wherein said porous support structure includes a porous polyethylene with an average pore size between 15 and 45 microns.

4. A perfusion chamber for an electrophysiology recording device, comprising:
    an impermeable shell;
    a permeable support structure contained within the shell;
    a holding well in the support structure for receiving a material subjected to an electrophysiologic experiment;
    an input port for supplying a perfusion solution to the material held in the well;
    an output port for removing the perfusion solution after flow through the permeable support structure; and
    a means for removing an excess of perfusion solution accumulated above a predetermined level in the chamber.

5. The chamber of claim 4, wherein said material is an oocyte.

6. The chamber of claim 4, wherein said support structure has a sloped top surface progressively converging downward toward the holding well.

7. The chamber of claim 4, wherein said holding well has a bottom surface conforming to a geometry of an oocyte.

8. The chamber of claim 7, wherein said geometry includes a spherical section.

9. The chamber of claim 4, wherein said permeable support structure includes a porous ceramic with an average pore size between 15 and 40 microns.

10. The chamber of claim 4, wherein said permeable support structure includes a porous polyethylene with an average pore size between 15 and 45 microns.

11. The chamber of claim 4, wherein said permeable support structure includes a porous material with an average pore size between 15 and 45 microns and has a sloped top surface progressively converging downward toward the holding well; and said holding well has a bottom surface conforming to a geometry of an oocyte.

12. The chamber of claim 11, wherein said geometry includes a spherical section; and said porous material is selected from the group consisting of a ceramic and a polyethylene material.

13. A holding chamber for microinjection and electrophysiological recording of a material, comprising:
    a housing;
    a support structure contained within the housing; and
    a holding well in the support structure for receiving a material subjected to testing;
        wherein the support structure has a sloped top surface progressively converging downward toward the holding well.

14. The chamber of claim 13, wherein said holding well has a bottom surface conforming to a geometry of an oocyte.

15. The chamber of claim 14, wherein said geometry includes a spherical section.

16. The chamber of claim 13, wherein said support structure includes a permeable material.

17. The chamber of claim 16, wherein said permeable material has an average pore size between 15 and 45 microns.

18. A holding chamber for microinjection and electrophysiological recording of an oocyte, comprising:
a housing;
a support structure contained within the housing; and
a holding well in the support structure for receiving an oocyte subjected to testing;
wherein the holding well has a bottom surface conforming to a geometry of the oocyte.

19. The chamber of claim 18, wherein said geometry includes a spherical section.

20. The chamber of claim 18, wherein said support structure includes a permeable material.

21. The chamber of claim 20, wherein said permeable material has an average pore size between 15 and 45 microns.

22. A method of perfusing a material in a chamber for an electrophysiology recording test, comprising the following steps:
providing a permeable support structure contained within an impermeable shell;
placing the material in a holding well in the support structure;
supplying a perfusion solution to the material held in the well;
removing the perfusion solution after flow through the permeable support structure; and
removing an excess of perfusion solution accumulated above a predetermined level in the chamber.

23. The method of claim 22, wherein the material is an oocyte cell.

24. The method of claim 22, wherein said supplying and removing steps are carried out using separate constant-flow pumps.

25. The method of claim 22, wherein said supplying step is carried out at a greater flow rate than said removing step.

26. A method of perfusing a material in a chamber for an electrophysiology recording test, comprising the following steps:
providing a support structure contained within a housing;
providing a holding well in the support structure for receiving a material subjected to an electrophysiologic experiment, said holding well having a bottom surface conforming to a geometry of the material;
placing the material in the holding well;
supplying a perfusion solution to the material held in the well; and
removing the perfusion solution from the chamber after interaction with the material.

27. The method of claim 26, wherein the material is an oocyte cell and said geometry includes a spherical section.

28. The method of claim 27, further comprising the step of inserting an electrode in the oocyte held in the holding well.

29. A method of perfusing a material in a chamber for an electrophysiology recording test, comprising the following steps:

providing a support structure contained within a housing, said support structure having a sloped top surface progressively converging downward toward a holding well;
placing the material on the support structure and allowing the material to move into the holding well by the action of gravity;
supplying a perfusion solution to the material held in the well; and
removing the perfusion solution from the chamber after interaction with the material.

30. The method of claim 29, wherein the holding well has a bottom surface conforming to a geometry of the material.

31. The method of claim 30, wherein the material is an oocyte cell and said geometry includes a spherical section.

32. The method of claim 31, further comprising the step of inserting an electrode in the oocyte held in the holding well.

33. A method of microinjecting an oocyte in a chamber in preparation for an electrophysiology recording test, comprising the following steps:
providing a support structure contained within a housing;
providing a holding well in the support structure for receiving an oocyte, said holding well having a bottom surface conforming to a geometry of the oocyte;
placing the oocyte in the holding well; and
microinjecting the oocyte in the holding well.

34. The method of claim 33, further comprising the steps of:
supplying a perfusion solution to the oocyte held in the well; and
removing the perfusion solution from the chamber after interaction with the oocyte.

35. The method of claim 34, further comprising the step of inserting an electrode in the oocyte held in the holding well.

36. A method of microinjecting a material in a chamber in preparation for an electrophysiology recording test, comprising the following steps:
providing a support structure contained within a housing, said support structure having a sloped top surface progressively converging downward toward a holding well;
placing the material on the support structure and allowing the material to move into the holding well by the action of gravity; and
microinjecting the material in the holding well.

37. The method of claim 36, further comprising the steps of:
supplying a perfusion solution to the material held in the well; and
removing the perfusion solution from the chamber after interaction with the material.

38. The method of claim 37, further comprising the step of inserting an electrode in the material held in the holding well.

39. The method of claim 36, wherein the holding well has a bottom surface conforming to a geometry of the material.

40. The method of claim 39, wherein the material is an oocyte cell and said geometry includes a spherical section.

* * * * *